United States Patent [19]

Klötzer et al.

[11] Patent Number: 4,908,363
[45] Date of Patent: Mar. 13, 1990

[54] IMIDAZOLE DERIVATIVES

[75] Inventors: Wilhelm Klötzer, Innsbruck; Renate Müssner, Nendeln, both of Austria; Marc Montavon, Basel, Switzerland; Nicolas Singewald, Innsbruck, Austria

[73] Assignee: Hoffmann-La Roche Inc., Nutley, N.J.

[21] Appl. No.: 169,207

[22] Filed: Mar. 15, 1988

[30] Foreign Application Priority Data

Mar. 20, 1987 [CH] Switzerland ............... 1073/87

[51] Int. Cl.⁴ ............... A61K 31/415; C07D 401/04; C07D 233/88
[52] U.S. Cl. ............... 514/235.8; 514/326; 514/397; 514/398; 544/139; 546/210; 548/336; 548/337
[58] Field of Search ............... 544/139; 546/210; 548/336, 337; 514/398, 397, 326, 235.8

[56] References Cited

U.S. PATENT DOCUMENTS 4,457,859 7/1984 Ivaschenko et al. ............... 548/337

FOREIGN PATENT DOCUMENTS 86-56429 of 1986 Australia .
0266532 5/1988 European Pat. Off. ............ 548/337

OTHER PUBLICATIONS

Chem. Abstracts 83(19):157710t (1975).
Chem. Abstracts 88(13): 83965j (1977).
Chem. Abstracts 99(23): 194874a (1983).
Coco, M. T. et al., Il Farmaco-Ed.Sc.-vol. 42, No. 5 (347-351) (Jun. 1986).
Derwent, #35,116 (G.E. 1,445,628) (1968).
Derwent, #806,39T-B (Fr. 2,122,395Q) (1971).
Derwent, #101,05U-B (Fr. 213 2632 Q) (1971).
Derwent, #31,566U-B (Be. 792606-Q) (1972).
Derwent, #74 452 E/36 (EP 59,090) (1981).
Derwent, #84-040274/07 (J5 9002-887-A) (1982).
Derwent, #84-290028/47 (EP 125,783A) (1983).
Derwent, #85-061999/10 (U.S. Pat. No. 4,500,540A) (1979).
Derwent, #85-019828/04 (Corresponds to EP 131,302-A) (1983).
Chem. Abstracts 102 (1985), Abst. No. 59125x.

*Primary Examiner*—Mary C. Lee
*Assistant Examiner*—Mary Sue Howard
*Attorney, Agent, or Firm*—George M. Gould; Bernard S. Leon; William G. Isgro

[57] ABSTRACT

Imidazole derivatives of the formula

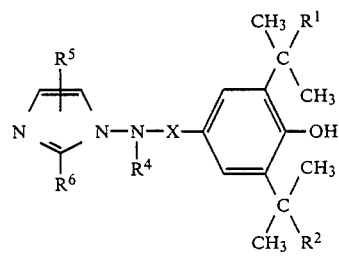

wherein $R^1$ and $R^2$ each is lower alkyl, X is a residue of the formula

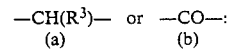

$R^3$ is hydrogen and $R^4$ is hydrogen or lower alkyl or $R^3$ and $R^4$ taken together are an additional carbon-nitrogen bond; $R^5$ is hydrogen or lower alkyl; $R^6$ is hydrogen, lower alkyl, lower alkylthio or a residue of the formula $-NR^7R^8$; and $R^7$ and $R^8$ each is lower alkyl or taken together with the nitrogen atom are a 5- or 6-membered saturated heterocycle; and pharmaceutically acceptable acid addition salts thereof are described. The compounds of formula I possess valuable pharmacodynamic properties, especially inflammation-inhibiting and edema-inhibiting properties, so that they can be used for the control or prevention of illnesses, especially for the control or prevention of inflammations and edemas.

26 Claims, No Drawings

IMIDAZOLE DERIVATIVES

BRIEF SUMMARY OF THE INVENTION

The present invention relates to imidazole derivatives of the formula

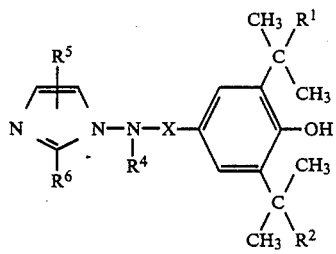

wherein $R^1$ and $R^2$ each is lower alkyl, X is a residue of the formula

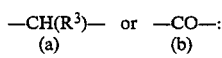

$R^3$ is hydrogen and $R^4$ is hydrogen or lower alkyl or $R^3$ and $R^4$ taken together are an additional carbon-nitrogen bond; $R^5$ is hydrogen or lower alkyl; $R^6$ is hydrogen, lower alkyl, lower alkylthio or a residue of the formula $-NR^7R^8$; and $R^7$ and $R^8$ each is lower alkyl or taken together with the nitrogen atom are a 5- or 6-membered saturated heterocycle, and pharmaceutically acceptable acid addition salts thereof.

DETAILED DESCRIPTION OF THE INVENTION

The invention relates to imidazole derivatives of the formula

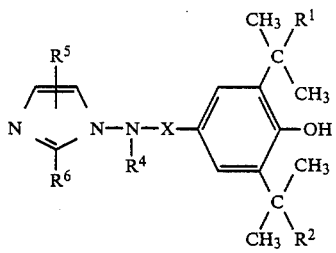

wherein $R^1$ and $R^2$ each is lower alkyl, X is a residue of the formula

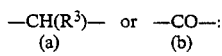

$R^3$ is hydrogen and $R^4$ is hydrogen or lower alkyl or $R^3$ and $R^4$ taken together are an additional carbon-nitrogen bond; $R^5$ is hydrogen or lower alkyl; $R^6$ is hydrogen, lower alkyl, lower alkylthio or a residue of the formula $-NR^7R^8$; and $R^7$ and $R^8$ each signify lower alkyl or taken together with the nitrogen atom are a 5- or 6-membered saturated heterocycle, and pharmaceutically acceptable acid addition salts thereof.

The compounds of formula I have been found to possess valuable pharmacodynamic properties, especially inflammation-inhibiting and edema-inhibiting properties, and can be used for the control or prevention of illnesses, especially for the control or prevention of inflammations and edemas.

Objects of the invention are the compounds of formula I and salts defined earlier, the preparation of said compounds and salts, medicaments containing such a compound or a salt thereof, the preparation of such medicaments, as well as the use of the compounds of formula I and salts defined earlier for the control or prevention of illnesses, especially in the control or prevention of inflammations and edemas, or the use of the compounds of formula I and salts defined earlier for the preparation of medicaments against inflammations and edemas.

As used herein, the term "lower alkyl" denotes straight-chain or branched saturated hydrocarbon residue of 1-7, preferably 1-4, carbon atoms such as methyl, ethyl, n-propyl, isopropyl, n-butyl, isobutyl, sec.-butyl, tert.-butyl and the like. The term "lower alkylthio" denotes a lower alkyl residue in the sense of the previous definition of the term "lower alkyl" attached via a sulfur atom. The term "5- or 6-membered saturated heterocycle" embraces residues such as 1-pyrrolidinyl, piperidino, morpholino and the like.

In formula I, conveniently $R^1$ and $R^2$ can each be methyl, $R^5$ can be hydrogen or methyl in the 4-position, $R^6$ can be hydrogen, methyl, n-propyl, isopropyl, methylmercapto or morpholino and $R^3$ can be hydrogen and $R^4$ can be hydrogen or methyl or $R^3$ and $R^4$ taken together can be an additional carbon-nitrogen bond.

Especially preferred compounds of formula I are:
1-(4-Hydroxy-3,5-di-tert.butylbenzylamino)imidazole;
1-(4-hydroxy-3,5-di-tert.butylbenzylideneamino)-2-methylimidazole; and
1-(4-hydroxy-3,5-di-tert.-butylbenzylideneamino)imidazole.

Preferred compounds of formula I are:
1-(4-Hydroxy-3,5-di-tert.-butylbenzylamino)-2-methylimidazole;
1-(4-hydroxy-3,5-di-tert.-butylbenzylamino)-2-propylimidazole; and
1-(4-hydroxy-3,5-di-tert.-butylbenzylamino)-2-methylmercaptoimidazole.

Additional representative compounds of formula I are:
1-(4-Hydroxy-3,5-di-tert.-butylbenzoylamino)-2-methylimidazole;
1-(4-hydroxy-3,5-di-tert.-butylbenzoylamino)imidazole;
1-(4-hydroxy-3,5-di-tert.-butylbenzylideneamino)-2-morpholinoimidazole;
1-(4-hydroxy-3,5-di-tert.-butylbenzylamino)-2-morpholinoimidazole;
1-(4-hydroxy-3,5-di-tert.-butylbenzylideneamino)-2-isopropylimidazole;
1-(4-hydroxy-3,5-di-tert.-butylbenzylideneamino)-4-methylimidazole;
1-(4-hydroxy-3,5-di-tert.-butylbenzylamino)-4-methylimidazole;
1-(4-hydroxy-3,5-di-tert.-butylbenzylideneamino)-2-propylimidazole; and
1-[N-(4-hydroxy-3,5-di-tert.-butylbenzyl)-N-methylamino]imidazole.

The imidazole derivatives of formula I of the invention and their pharmaceutically acceptable acid addition salts can be prepared in accordance with the invention by (a) condensing a compound of the formula

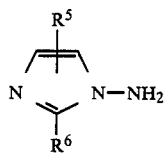

wherein $R^5$ and $R^6$ have the above significance, with an aldehyde of the formula

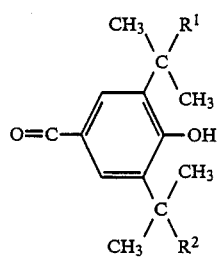

wherein $R^1$ and $R^2$ have the above significance; or (b) acylating a compound of the formula

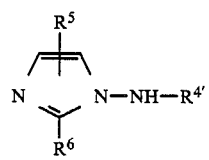

wherein $R^5$ and $R^6$ have the above significance and $R^{4'}$ is hydrogen or lower alkyl, with a reactive derivative of a carboxylic acid of the formula

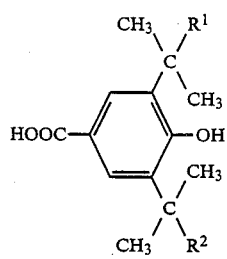

wherein $R^1$ and $R^2$ have the above significance; or (c) reducing a compound of the formula

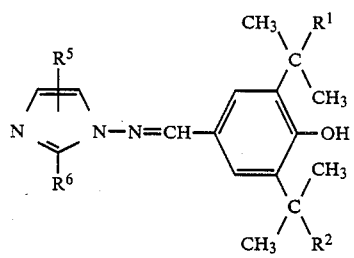

wherein $R^1$, $R^2$, $R^5$ and $R^6$ have the above significance; or (d) reducing a compound of the formula

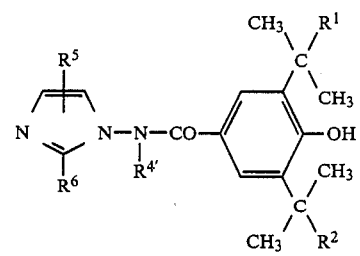

wherein $R^1$, $R^2$, $R^{4'}$, $R^5$ and $R^6$ have the above significance; or (e) N-alkylating a compound of the formula

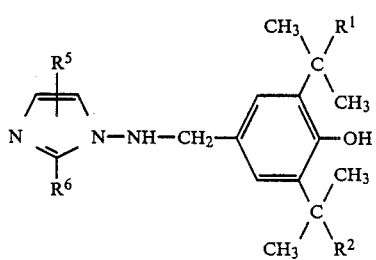

wherein $R^1$, $R^2$, $R^5$ and $R^6$ have the above significance; or (f) dehydrogenating a compound of formula Ic above; or (g) removing the alkylthio group from a compound of the formula

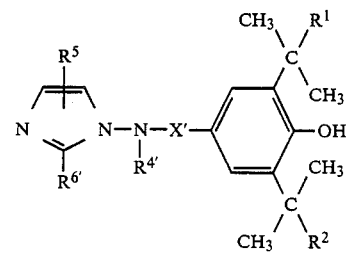

wherein $R^1$, $R^2$, $R^{4'}$ and $R^5$ have the above significance and $X'$ is methylene or carbonyl and $R^{6'}$ is lower alkylthio; or (h) converting a compound of formula I into a pharmaceutically acceptable acid addition salt.

For aspect (a) of the process in accordance with the invention, as starting materials of formula II, there can be used, for example, 1-aminoimidazole, 1-amino-2-methylimidazole and the like and as the starting material of formula III, there can be used, for example, 4-hydroxy-3,5-di-tert.-butylbenzaldehyde. The reaction is effected in an organic solvent which is inert under the reaction conditions, for example, a lower alkanol such as methanol, ethanol or the like. Furthermore, it is convenient to carry out the condensation of the compounds of formula II with the compounds of formula III in the presence of an acid. This can be achieved by adding to the reaction mixture a corresponding amount of a suitable acid, for example hydrochloric acid, or by using the starting material of formula II in the form of an acid addition salt, for example, as the hydrochloride. The condensation is conveniently effected at room temperature and normal pressure. The reaction time is in the range from to one to a few (a maximum of about 12) hours.

The reactive derivatives of the carboxylic acids of formula V, which can be used as starting materials in aspect (b) of the process in accordance with the invention, comprise preferably the acid halides, for example, acid chlorides; however, other reactive derivatives, for example mixed anhydrides and the like, also come into consideration. Depending on the nature of the reactive derivative of a carboxylic acid of formula V used, the starting material of formula IV can be used as the free base or in the form of an acid addition salt, for example, in the form of the hydrochloride. For instance, 1-aminoimidazole hydrochloride, 1-amino-2-methylimidazole hydrochloride or the like can be heated with 4-hydroxy-3,5-di-tert.-butylbenzoyl chloride without the addition of a solvent for about a half to one hour to a temperature of about 180°–250° C. (conveniently 200°–210° C.), whereby the mixture melts with the evolution of gaseous hydrogen chloride.

The reduction of a compound of formula Ia in accordance with aspect (c) of the process in accordance with the invention can be effected, for example, by catalytic hydrogenation, conveniently in the presence of a palladium catalyst or the like. The catalytic hydrogenation is conveniently effected in a solvent which is inert under the reaction conditions, for example, in a lower alkanol such as methanol or the like, or in a mixture of a water-miscible organic solvent and water, for example, in aqueous methanol or the like; the addition of an acid such as hydrochloric acid is convenient. The catalytic hydrogenation is conveniently carried out at room temperature and normal pressure. Usually, the hydrogenation has finished after one to a few hours.

The reduction of the compounds of formula Ia can, however, also be carried out utilizing complex hydrides, for example, by means of sodium cyanoborohydride or the like. When sodium cyanoborohydride is used as the reducing agent, then glacial acetic acid primarily comes into consideration as the solvent. In this embodiment, the reduction is conveniently carried out at room temperature and normal pressure. The reaction time for the reduction of a compound of formula Ia by means of a complex metal hydride takes several, conveniently about 12, hours.

The reduction in accordance with the invention of a compound of formula Ia in accordance with aspect (c) of the process in accordance with the invention yields corresponding compound of formula Ic.

The reduction of a compound of formula Ib in accordance with aspect (d) of the process in accordance with the invention can be effected conveniently by means of a reducing agent derived from boron hydride, for example, by means of borane-dimethyl sulfide complex. As the reaction medium, there come into consideration anhydrous organic solvents or solvent mixtures which are inert under the reaction conditions, for example, mixtures of tetrahydrofuran and toluene or the like. The reaction is conveniently effected at an elevated temperature, for example, at the reflux temperature of the reaction system, and the reaction time comprises a few (for example, about 4) hours.

The N-alkylation of a compound of formula Ic in accordance with aspect (e) of the process in accordance with the invention is conveniently carried out initially by appropriately N-acylating the starting material and thereupon reducing the thus-introduced acyl group to the desired alkyl group. When it is desired to N-methylate a compound of formula Ic in this manner, then in a first step a compound of formula Ic is converted into the corresponding N-formyl compound, whereupon in a second step the formyl group is reduced to the methyl group. The N-formylation can be carried out, according to a first embodiment, by reacting acetic anhydride and formic acid with one another, taking up the mixed anhydride formed with a suitable inert organic solvent such as tetrahydrofuran or the like, introducing a compound of formula Ic into the solution obtained and leaving the reaction mixture to stand at room temperature for one to a few hours. According to another embodiment, a compound of formula Ic can be dissolved in formic acid. Thereupon, acetic acid is added and the mixture left to stand overnight.

The reduction of the thus-obtained N-formyl compound is conveniently effected by means of a reducing agent derived from boron hydride, for example, by means of borane-dimethyl sulfide complex. This reduction is conveniently effected in an anhydrous organic solvent or solvent mixture which is inert under the reaction conditions, for example, in a mixture of tetrahydrofuran and toluene or the like. The reduction takes a few (about 4) hours and is conveniently effected at an elevated temperature, for example, at the reflux temperature of the reaction system.

The dehydrogenation of a compound of formula Ic in accordance with aspect (f) of the process in accordance with the invention yields a corresponding compound of formula Ia and is effected using agents which are customary for such dehydrogenations, such as dicyanodichlorobenzoquinone, chloranil, diethyl azodicarboxylate and the like. The reaction conditions can vary depending on the dehydrogenating agent which is used, but in principle are familiar to any person skilled in the art. For example, when dicyanodichlorobenzoquinone is used as the dehydrogenating agent, then the dehydrogenation is conveniently carried out in an organic solvent which is inert under the reaction conditions, for example, in an aromatic hydrocarbon such as benzene, toluene, xylene or the like, advantageously in the presence of small amounts of an anhydrous acid such as acetic acid or the like. The dehydrogenation takes about 10 minutes to 1 hour and is effected at an elevated temperature, conveniently at or slightly below the reflux temperature of the reaction system.

The cleavage of a lower alkylthio group from a compound of formula Id in accordance with aspect (g) of the process in accordance with the invention is carried out using methods which are known and are familiar to the person skilled in the art. For example, a compound of formula Id is dissolved in an organic solvent which is inert under the reaction conditions, for example, in a lower alkanol such as methanol, and than there is added a nickel(II) salt such as nickel(II) chloride.6$H_2O$. Subsequently, a complex boron hydride compound such as sodium borohydride is added and the reaction mixture is then left to stand at room temperature until the reduction has finished, which takes a few (about 2–5) hours. However, the cleavage of a lower alkylthio group from a compound of formula Id can also be effected, for example, by means of Raney-nickel, conveniently in ethanol or the like, at a temperature of about 50° to 75° C., which likewise takes a few, for example, two hours.

In accordance with aspect (h) of the process in accordance with the invention a compound of formula I can be converted into a corresponding acid addition salt by reaction with an organic or inorganic acid. Acids which form pharmaceutically acceptable salts, for example, are hydrogen chloride, hydrogen bromide, phosphoric acid, sulfuric acid, citric acid, p-toluenesulfonic acid and the like.

The starting materials of formula II are known or can be prepared readily according to methods which are known and which are familiar to a person skilled in the art. Moreover, many of the Examples hereinafter contain detailed information concerning the preparation of particular compounds of formula II. Compounds of formula IV wherein $R^{4'}$ is lower alkyl can be prepared by N-alkylating corresponding compounds of formula II in analogy to the N-alkylation of compounds of formula Ic in accordance with process variant (e) of the process in accordance with the invention.

As mentioned earlier, the imidazole derivatives of formula I and their pharmaceutically acceptable acid addition salts possess valuable pharmacodynamic properties. The compounds of formula I can be used in the control or prevention of inflammations and edemas, for example, they can be used as anti-inflammatory agents in the treatment of inflammatory joint diseases, such as, arthritis.

Representative compounds of formula I were tested for their inflammation-inhibiting properties in the animal test described hereinafter:

0.1 ml of a 0.5% (weight/volume) suspension of heat-killed and dried Mycobacterium butyricum in heavy mineral oil, containing 0.2% digitonin, is injected into the base of the tail of male rats (120–140 g). The animals are housed individually and receive feed and water ad libitum. The thus-produced arthritis is allowed to develop without treatment during 21 days. Then on the one hand the body weight of the animals is determined and on the other hand the volumes of their two hind paws (by immersing the paws in a mercury plethysmograph up to the height of the lateral malleolus). Thereupon, the animals are divided into groups each comprising six animals in each case of approximately the same average volumes of the hind paws. The substance to be investigated is then administered to them by intubation each day over a period of 7 days. At the end of the treatment period, body weight and volumes of the hind paws are again determined and the changes over the treatment period is calculated. Subsequently, the animals are killed and plasma samples are removed from them in order to determine the fibrinogen in accordance with Exner et al., 1979 (Amer. J. Clin. Path.) after precipitation with ammonium sulfate.

The results determined for three representative compounds of formula I, in the animal test described hereinbefore, are set forth in the following Table I.

TABLE 1

| Compound | Dosage ($\mu$ mol/kg) | Inflammation-inhibiting activity | | Body weight change (g) |
|---|---|---|---|---|
| | | Paw volume change (ml) | Plasma Fibrinogen (mg/dl) | |
| Vehicle (Tween/80) | — | 0.46 ± 0.08 | 1233 ± 56 | 13.2 ± 1.8 |
| A | 66 | −0.18 ± 0.08* | 1040 ± 75* | 30.5 ± 1.2* |
| B | 66 | −0.84 ± 0.12* | 75 ± 15* | 35.3 ± 1.8* |
| | 22 | −0.77 ± 0.05* | 405 ± 126* | 28.2 ± 1.4* |

TABLE 1-continued

| Compound | Dosage ($\mu$ mol/kg) | Inflammation-inhibiting activity | | Body weight change (g) |
|---|---|---|---|---|
| | | Paw volume change (ml) | Plasma Fibrinogen (mg/dl) | |
| C | 66 | −0.92 ± 0.08* | 544 ± 97* | 31.2 ± 2.0* |

*Values Value significantly different from the corresponding value for animals treated with vehicle (p < 0.05; Students t-Test).
A = 1-(4-Hydroxy-3,5-di-tert.-butylbenzylamino)imidazole.
B = 1-(4-Hydroxy-3,5-di-tert.butylbenzylideneamino)-2-methylimidazole.
C = 1-(4-Hydroxy-3,5-di-tert.-butylbenzylideneamino)-imidazole.

The following Table II contains data concerning the acute toxicity of the above three compounds ($LD_{50}$ in the case of single oral administration to mice).

TABLE II

| Compound | A | B | C |
|---|---|---|---|
| $LD_{50}$ (mg/kg p.o.) | >1000 | >1000 | >1000 |

Furthermore, compound A above as well as the following two compounds, likewise embraced by formula I, -D = 1-(4-hydroxy-3,5-di-tert.-butylbenzylamino)-2-methylimidazole and
-E = 1-(4-hydroxy-3,5-di-tert.butylbenzylamino)-2-propylimidazole were tested for their edema-inhibiting properties in the animal test described hereinafter:

A pleuritis is produced in male rats (230–250 g), which receive feed and water ad libitum, by the injection of 0.2 ml of a 1% solution of carrageen in sterile, pyrogen-free sodium chloride solution into the right pleural cavity. The substance to be investigated, suspended in an aqueous vehicle (containing 0.5% carboxymethylcellulose, 0.9% sodium chloride, 0.37% Tween 80 and 0.86% benzyl alcohol), or the vehicle alone, are administered by intubation to the animals 1 hour before and 5 hours after the carrageen injection. Twenty-four (24) hours after the carrageen injection, the animals are killed by decapitation, left to bleed out and the pleural cavity is exposed by cutting through the ribs on both sides of the sternum. The exudate is removed from the pleural cavity by means of a pipette and its volume is determined. Thereupon, the pleural cavity is washed once with phosphate-buffered sodium chloride solution containing fetal bovine serum (1:1) and the wash solution is combined with the exudate. The total number of cells in the pleural cavity is determined using a "Coulter Counter" which is calibrated so that red blood corpuscles are not counted. Cell smears on glass plates can be produced directly from the exudate, fixed in methanol and colored for the differential counting of polymorphonuclear leucocytes (PMN) and macrophages; a total of 200 PMN and macrophages can be counted and the results expressed as a percentage of each type of cell present in the pleural exudate.

The results of the previously described test are reproduced in the following Table III:

TABLE III

| Compound | Dosage (mg/kg p.o.) | % Chance compared with controls | |
|---|---|---|---|
| | | Exudate volume | Number of cells |
| A | 100 | −68* | −23* |
| | 50 | −60* | −14* |
| | 30 | −51* | −12 |

TABLE III-continued

| Compound | Dosage (mg/kg p.o.) | % Chance compared with controls | |
|---|---|---|---|
| | | Exudate volume | Number of cells |
| D | 100 | −60* | −22 |
| | 30 | −29* | −6 |
| E | 100 | −73* | −21* |
| | 30 | −39* | +4 |

*Value significantly different from the corresponding value for animals treated only with vehicle (p < 0.05; Students t-Test)

The compounds of formula I and their pharmaceutically acceptable acid addition salts can be used as medicaments, for example, in the form of pharmaceutical preparations. The pharmaceutical preparations can be administered orally, for example, in the form of tablets, coated tablets, dragees, hard and soft gelatine capsules, solutions, emulsions or suspensions. However, the administration can also be effected rectally, for example, in the form of suppositories, or parenterally, for example, in the form of solutions for injection.

For the preparation of pharmaceutical dosage forms, the compounds of formula I and their pharmaceutically acceptable acid addition salts can be processed with pharmaceutically inert, inorganic or organic carriers. Lactose, maize starch or derivatives therof, talc, stearic acid or its salts and the like can be used, for example, as carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active substance, no carriers are, however, required in the case of soft gelatin capsules. Suitable carriers for the preparation of solutions and syrups are, for example, water, polyols, saccharose, invert sugar, glucose and the like. Suitable carriers for injection solutions are, for example, water, alcohols, polyols, glycerol, vegetable oils and the like. Suitable carriers for suppositories are, for example, natural or hardened oils, waxes, fats, semi-liquid or liquid polyols and the like.

The pharmaceutical preparations can also contain preserving agents, solubilizers, stabilizing agents, wetting agents, emulsifying agents, sweetening agents, coloring agents, flavoring agents, salts for varying the osmotic pressure, buffers, coating agents or antioxidants. In addition, they can also contain other therapeutically valuable substances.

As mentioned earlier, medicaments containing a compound of formula I or a pharmaceutically acceptable acid addition salt thereof and a therapeutically inert excipient are likewise an object of the invention, as is a process for the preparation of such medicaments which comprises bringing one or more compounds of formula I or pharmaceutically acceptable acid addition salts thereof and, if desired, one or more other therapeutically valuable substances into a galenical administration form together with one or more therapeutically inert excipients.

As mentioned earlier, the compounds of formula I and their pharmaceutically acceptable acid addition salts can be used in accordance with the invention in the control or prevention of illnesses, especially in the control or prevention of inflammations and edemas. The dosage can vary within wide limits and will, of course, be adjusted to the individual requirements in each particular case. In general, in the case of oral administration a daily dosage of about 10 mg to 2000 mg comes into consideration.

As mentioned earlier, the use of the compounds of formula I and their pharmaceutically acceptable acid addition salts for the preparation of medicaments, especially of medicaments against inflammations and edemas, is also an object of the invention.

The Examples which follow further illustrate the invention. All temperatures are given in degrees Celsius, unless otherwise stated.

EXAMPLE 1

(a) 5 g of hydroxylamine O-sulfonic acid are dissolved in 30 ml of water and neutralized with 3.7 g of sodium bicarbonate while cooling with ice. This solution is added dropwise to a solution of 3.63 g of 2-methylimidazole in 15 ml of water. The mixture is stirred at room temperature for about 20 hours and then acidified with 13 ml of 2N hydrochloric acid until the pH of the solution is 1. The solution is treated with two spatula tips of active carbon, stirred for 15 minutes, filtered and the clear filtrate is treated with 5 ml of benzaldehyde and 10 ml of ether. Thereupon, the mixture is stirred for 6 hours, cooled in an ice-bath for 15 minutes and the separated solid is removed by filtration. The filtrate is treated as described below.

After reprecipitation of the solid from methanol/ether there is obtained 1,3-bis(benzylideneamino)-2-methylimidazolium chloride of m.p. 244°–249°.

The above filtrate is extracted three times with 15 ml of ether each time. The aqueous phase is neutralized (pH 7) with 9 ml of 4N sodium hydroxide solution while cooling. The precipitate is removed by filtration, reprecipitated from methanol/ether and there is obtained 1-benzylideneamino-2-methylimidazole of m.p. 122°–124°.

(b) 3.24 g of 1,3-bis(benzylideneamino)-2-methylimidazolium chloride are dissolved in 50 ml of methanol. The solution is cooled to 0° (internal temperature) and treated while stirring with a solution of 2.6 g of potassium cyanide in 8 ml of water, whereby the temperature is not allowed to rise substantially. After 15 minutes, the methanol is removed by evaporation in a vacuum at the lowest possible temperature. The residue is diluted with 30 ml of water, whereupon the mixture is extracted three times with chloroform. The dried chloroform extract is evaporated and there is obtained 1-benzylideneamino-2-methylimidazole of m.p. 125°.

(c) 7.4 g of 1-benzylideneamino-2-methylimidazole are suspended in 50 ml of water. The suspension is acidified (pH=1–2) with 25 ml of 2N hydrochloric acid and then subjected to a steam distillation until benzaldehyde no longer passes over. The residual clear solution is evaporated to dryness and the oily evaporation residue is crystallized with ether at 0°. The crystals obtained are reprecipitated from ethanol/ether and there is obtained 1-amino-2-methylimidazole hydrochloride of m.p. 139°–141°.

(d) 5.35 g of 1-amino-2-methylimidazole hydrochloride are dissolved in 300 ml of ethanol, whereupon 9.3 g of 4-hydroxy-3,5-di-tert.-butylbenzaldehyde are added. The mixture is stirred at room temperature for 1 hour and then evaporated in a vacuum. 150 ml of ice-water and 200 ml of methylene chloride are added to the residue and the mixture is neutralized (pH=7) with saturated sodium bicarbonate solution. The methylene chloride phase is separated and the aqueous phase is extracted with 100 ml of methylene chloride. The combined methylene chloride phases are dried and evaporated. The residue is stirred with ether and filtered. The filter residue is dried at 80° in a vacuum and there is obtained 1-(4-hydroxy-3,5-di-tert.-butylbenzylideneamino)-2-methylimidazole of m.p. 206°–207°.

EXAMPLE 2

3.13 g of 1-(4-hydroxy-3,5-di-tert.-butylbenzylideneamino)-2-methylimidazole are dissolved in 100 ml of methanol, whereupon 0.5 g of palladium catalyst (5% on carbon) and 10 ml of 1N hydrochloric acid are added and the mixture is then hydrogenated at normal pressure and room temperature. After 240 ml of hydrogen have been taken up, the catalyst removed by filtration and the filtrate is evaporated. The oily residue is taken up with 50 ml of water and saturated sodium bicarbonate solution is added up to a neutral reaction (pH=7). The separated residue is removed by filtration and taken up in 100 ml of methylene chloride. The methylene chloride solution is washed with 50 ml of water, dried and evaporated. The residue is stirred with ether, filtered and there is obtained crude 1-(4-hydroxy-3,5-di-tert.-butylbenzylamino)-2-methylimidazole of m.p. 181°–182°. A pure product of m.p. 182°–183° is obtained by recrystallization from acetonitrile.

EXAMPLE 3

1.0 g of 1-amino-2-methylimidazole hydrochloride and 2.0 g of 4-hydroxy-3,5-di-tert.-butylbenzoyl chloride are mixed and heated on an oil-bath for 40 minutes to 200°–210° (bath temperature), whereby the flask content melts with the evolution of HCl and then again becomes solid. The cooled flask content is dissolved in 30 ml of water, whereupon the solution is filtered and the filtrate is adjusted to pH 9 with 10% sodium carbonate solution. The separated precipitate is removed by filtration and dissolved in 25 ml of hot ethanol, whereupon the still hot solution is treated with 10 ml of water. After cooling, the separated solid is removed by filtration and recrystallized from ethyl acetate. There is obtained 1-(4-hydroxy-3,5-di-tert.-butylbenzoylamino)-2-methylimidazole of m.p. 322°–324° (dec.).

EXAMPLE 4

A suspension of 200 mg of 1-(4-hydroxy-3,5-di-tert.-butylbenzoylamino)-2-methyl-1H-imidazole in 10 ml of anhydrous tetrahydrofuran is treated under an inert gas with 1.2 ml of a 2N borane-dimethyl sulfide complex solution in toluene. The mixture is then heated at reflux for 4 hours, left to cool to 0°, treated with methanolic hydrochloric acid (5 ml of methanol and 0.5 ml of conc. HCl), and again heated at reflux for 1 hour and evaporated in a vacuum. The residue is taken up in 4 ml of water and saturated sodium bicarbonate solution is added until the pH amounts to 8–9. The mixture is extracted three times with 5 ml of methylene chloride each time and, after drying, the combined methylene chloride phases are evaporated. The residue is recrystallized from cyclohexane and there is obtained 1-(4-hydroxy-3,5-di-tert.-butylbenzylamino)-2-methylimidazole of m.p. 180°.

EXAMPLE 5

(a) 22.6 g of hydroxylamine O-sulfonic acid are dissolved in 60 ml of ice-water and neutralized (pH=6) with about 18 g of sodium bicarbonate. A solution of 27.2 g of imidazole in 60 ml of water is added dropwise within 45 minutes while stirring. The mixture is stirred at room temperature for about 20 hours and then acidified to pH 1–2 with about 160 ml of 2N hydrochloric acid while cooling with ice. Thereupon, the dark solution is stirred with active carbon for 15 minutes, filtered and the clear filtrate is treated with 28 ml of benzaldehyde and 30 ml of ether. Thereupon, the mixture is stirred for 18 hours. The resulting suspension is then cooled for 15 minutes and the separated 1,3-bis(benzylideneamino)imidazolium chloride is removed by filtration.

The filtrate is extracted three times with 40 ml of ether each time. The aqueous, acidic phase is then neutralized to pH 7 with 40 ml of 4N sodium hydroxide solution while cooling with ice. The separated precipitate is extracted once with 100 ml of chloroform and twice more with 20 ml of chloroform each time. The combined chloroform phases are dried over sodium sulfate and evaporated. The evaporation residue is dissolved in ethanol while warming, whereupon the solution is treated with hot water in an amount such that turbidity does not occur. The mixture is subsequently filtered rapidly and left to cool. After cooling in ice for 1 hour the separated 1-benzylideneaminoimidazole is removed by filtration.

(b) In an analogous manner to that described in Example 1b), from 1,3-bis(benzylideneamino)imidazolium chloride there is obtained 1-benzylideneaminoimidazole of m.p. 115°.

(c) 8.68 g of 1-benzylideneaminoimidazole are suspended in 50 ml of water, whereupon the suspension is acidified (pH=1–2) with 28 ml of 2N hydrochloric acid and then subjected to a steam distillation until benzaldehyde no longer passes over. Thereafter, the residual clear solution is evaporated to dryness in a vacuum at 50°–60° and the evaporation residue is crystallized at 0° with ether. After recrystallization of the crystallizate from ethanol/ether, there is obtained 1-aminoimidazole hydrochloride of m.p. 102°.

(d) 0.48 g of 1-aminoimidazole hydrochloride are suspended in 30 ml of ethanol, whereupon 0.93 g of 4-hydroxy-3,5-di-tert.-butylbenzaldehyde is added. The suspension is stirred at room temperature for 3 hours, whereby there results a clear solution which is evaporated in a vacuum. The residue is taken up in 15 ml of water, neutralized (pH=7) with ice-cold saturated sodium bicarbonate solution and extracted rapidly three times with 30 ml of methylene chloride each time. The combined organic phases are dried over sodium sulfate, filtered and evaporated in a vacuum. By sublimation of the residue (160°/12 Torr), there is obtained 1-(4-hydroxy-3,5-di-tert.-butylbenzylideneamino)imidazole of m.p. 171°–174°.

EXAMPLE 6

0.9 g of 1-(4-hydroxy-3,5-di-tert.-butylbenzylideneamino)imidazole are suspended in 10 ml of glacial acetic acid and treated with 1.61 g of sodium cyanoborohydride, whereby a solution results. The solution is stirred at room temperature overnight and then evaporated in a vacuum. The residue is treated with 10 ml of water, neutralized (pH=7) with ice-cold saturated sodium bicarbonate solution and extracted three times with 30 ml of methylene chloride each time. The combined organic phases are dried over sodium sulfate, filtered and evaporated in a vacuum. The residue is crystallized with ehter. The product is removed by filtration and reprecipitated from ethanol/water. There is obtained 1-(4-hydroxy-3,5-di-tert.-butylbenzylamino)imidazole of m.p. 171°–174°.

EXAMPLE 7

28.7 g of 1-(4-hydroxy-3,5-di-tert.-butylbenzylideneamino)imidazole are dissolved in 500 ml of methanol, whereupon 96 ml of 1N hydrochloric acid and 3 g of palladium/carbon are added and the mixture is hydrogenated at normal pressure and room temperature. After 2.2 l of hydrogen have been taken up, the catalyst is removed by filtration and the filtrate is evaporated. Eight hundred (800) ml of methylene chloride and 300 ml of water are added to the residue. The mixture is neutralized (pH=7) with saturated sodium bicarbonate solution while agitating. Then, the methylene chloride phase is separated and the aqueous phase is extracted twice with 100 ml of methylene chloride each time. The methylene chloride phases are combined, dried and evaporated. The residue is recrystallized from ethanol/water (3:1), and there is obtained 1-(4-hydroxy-3,5di-tert.-butylbenzylamino)imidazole of m.p. 178°–180°.

EXAMPLE 8

1.20 g of 1-aminoimidazole hydrochloride are melted together with 2.70 g of 4-hydroxy-3,5-di-tert.-butylbenzoyl chloride on an oil-bath (about 200°–210° bath temperture), whereby a vigorous gas evolution occurs. After 40 minutes, the solid residue is triturated with hot diisopropyl ether and filtered. The filter residue is taken up in water, treated with saturated sodium bicarbonate solution up to an alkaline reaction and extracted three times with methylene chloride. The combined organic extracts are dried over anhydrous magnesium sulfate, filtered and evaporated under reduced pressure on a rotary evaporator. The residue is taken up in ethyl acetate, heated and the 1-(4-hydroxy-3,5-di-tert.-butylbenzoylamino)imidazole is precipitated while hot with n-hexane. The precipitate is removed by filtration, washed once with n-hexane/ethyl acetate (2:1) and dried at 50° in a high vacuum; m.p. 245° (dec.).

EXAMPLE 9

1-(4-Hydroxy-3,5-di-tert.-butylbenzylamino)imidazole can be obtained from 1-(4-hydroxy-3,5-di-tert.-butylbenzoylamino)imidazole in analogy to the details in Example 4.

EXAMPLE 10

(a) A solution of 120 ml of carbon disulfide and 60.6 g of dicyclohexycarbodiimide in 300 ml of tetrahydrofuran is cooled to −8° with an ice/salt mixture. Thereupon, 39.9 g of aminoacetaldehyde diethyl acetal are added dropwise while stirring so that the temperature of the reaction mixture does not exceed −5° (approximately 1 hour). The mixture is then warmed slowly to room temperature while stirring (approximately 2 hours) and left to stand overnight. The resulting precipitate (dicyclohexylthiourea) is then removed by filtration and washed thoroughly with n-hexane. The filtrate is concentrated in a vacuum and the separated dicyclohexylthiourea is again removed by filtration and washed with n-hexane. This procedure is repeated until dicyclohexylthiourea no longer separates upon concentration. Finally, the filtrate is freed completely from solvents. The residue is distilled at 11 Torr (bath temperature 130°–134°), whereby there is obtained 2,2-diethoxyethyl isothiocyanate in the form of a colorless oil; b.p. 100°/11 Torr.

(b) 2.5 g of hydrazine hydrate (98–100%) are dissolved in 10 ml of 96% ethanol. This solution is treated dropwise while stirring with 8.75 g of 2,2-diethoxyethyl isothiocyanate in such a manner that the temperature does not exceed 40°. After completion of the addition and cooling, the flask content solidifies completely. The ethanol is removed by evaporation in a vacuum at 30°–40° (bath temperature). The 4-(2′,2′-diethoxyethyl)-thiosemicarbazide (m.p. 92°–97°) which remains behind as a colorless crystalline residue can be processed without purification. A sample recrystallized from water exhibits a melting point of 95°–97°.

(c) 2.07 g of 4-(2′,2′-diethoxyethyl)thiosemicarbazide are treated with 10 ml of 2N sulfuric acid and heated on a boiling water-bath under reflux for 15 minutes. The yellowish solution is then treated at about 40° with 1.06 g of benzaldehyde and stirred well. After cooling to room temperature the resulting yellow precipitate is removed by filtration, washed with water and dried. For purification, the crude product is suspended in about 15 ml of hot water and treated while hot with sufficient ethanol so that complete solution occurs. This solution is filtered while hot and subsequently cooled. 1-Benzylideneamino-2-mercaptoimidazole thereby separates in the form of yellow needles. A sample is dried for 12 hours at 40° and 10 Torr and then exhibits a m.p. of 158°–161°.

(d) 10.16 g of 1-benzylideneamino-2-mercaptoimidazole are suspended in 30 ml of absolute ethanol and treated with a solution of 1.15 g of sodium in 70 ml of absolute ethanol. After the addition of 7.1 g of methyl iodide, the reaction mixture is stirred at room temperature for 3 hours. For the work-up, the resulting yellow solution is concentrated to a quarter and 100 ml of water are added. The resulting crystalline crude product is removed by filtration, washed three times with water and recrystallized from methanol/water. There is obtained 1-benzylideneamino-2-methylmercaptoimidazole of m.p. 95°–97°.

(e) 2.17 g of 1-benzylideneamino-2-methylmercaptoimidazole are suspended in 50 ml of water and, after the addition of 6 ml of 2N hydrochloric acid, subjected to a steam distillation. After completion of the cleavage of benzaldehyde, the resulting solution is concentrated to a few ml, 5N sodium hydroxide solution is added up to an alkaline reaction and the mixture is extracted five times with 15 ml of methylene chloride each time. The combined methylene chloride phases are dried over sodium sulfate, filtered and evaporated. The crystalline residue is recrystallized from n-hexane/ethyl acetate and there is obtained 1-amino-2-methylmercaptoimidazole in the form of colorless crystals of m.p. 71°–73° (subl. from about 50°).

(f) 0.65 g of 1-amino-2-methylmercaptoimidazole are dissolved in 50 ml of methanol and treated with 3 ml of 2N hydrochloric acid. After the addition of 1.05 g of 4-hydroxy-3,5-di-tert.-butylbenzaldehyde, the reaction mixture is stirred at room temperature overnight. Subsequently, the solvent is removed by evaporation in a vacuum. The residue is suspended in 30 ml of water and treated with saturated sodium carbonate solution up to an alkaline reaction. The mixture is extracted three times with 20 ml of methylene chloride each time, the combined organic phases are dried over sodium sulfate, filtered and evaporated. The crystalline residue is recrystallized from water/methanol, and there is obtained 1-(4-hydroxy-3,5-di-tert.-butylbenzylideneamino)-2-methylmercaptoimidazole of m.p. 181°–183°.

EXAMPLE 11

1.04 g of 1-(4-hydroxy-3,5-di-tert.-butylbenzylideneamino)-2-methylmercaptoimidazole are dissolved in 20 ml of glacial acetic acid and treated portionwise within 30 minutes with 0.43 g of 90% sodium cyanoborohydride. The reaction mixture is stirred at room temperature overnight, whereupon the solvent is removed by evaporation in a vacuum and the residue is taken up with 20 ml of water. Saturated sodium carbonate solution is added up to an alkaline reaction and the mixture is extracted three times with 15 ml of methylene chloride each time. The combined organic phases are dried over sodium sulfate, filtered and evaporated. The residue is recrystallized from methanol/water and there is obtained 1-(4-hydroxy-3,5-di-tert.-butylbenzylamino)-2-methylmercaptoimidazole of m.p. 110°–113°.

EXAMPLE 12

Variant (a): 200 mg of 1-(4-hydroxy-3,5-di-tert.-butylbenzylamino)-2-methylmercaptoimidazole are dissolved in 8 ml of ethanol together with 0.41 g of nickel-(II) chloride.6$H_2O$. This solution is cooled in an ice-bath and 0.7 g of sodium borohydride is added portionwise within 1 hour. After completion of the addition, the ice-bath is removed and the black reaction mixture is stirred at room temperature for an additional 4 hours. For the work-up, the mixture is again cooled and sufficient 2N hydrochloric acid is added so that the reaction mixture has an acidic reaction. The resulting mixture is stirred for a few minutes and treated with conc. ammonia up to an alkaline reaction. Subsequently, the mixture is filtered through a bed of siliceous earth and the filter cake is washed five times with methylene chloride. The organic phase of the filtrate is separated, washed twice with water, dried over sodium sulfate and evaporated. The crystalline residue is reprecipitated from methanol/water and there is obtained 1-(4-hydroxy-3,5-di-tert.-butylbenzylamino)imidazole in the form of colorless crystals of m.p. 171°–174°.

Variant (b): 600 mg of 1-(4-hydroxy-3,5-di-tert.-butylbenzylamino)-2-methylmercaptoimidazole dissolved in 20 ml of ethanol are heated to 60°–70° for 2 hours while stirring with a 5-fold amount by weight of ethanol-moist Raney-nickel W2. The nickel is then removed by filtration and boiled up twice with 10 ml of ethanol each time. The combined alcoholic filtrates are evaporated, and 1-(4-hydroxy-3,5-di-tert.-butylbenzylamino)imidazole is obtained as the residue in the form of colorless crystals of m.p. 171°–174°.

EXAMPLE 13

300 mg of 1-(4-hydroxy-3,5-di-tert.-butylbenzylamino)imidazole are heated to about 60°–70° on a water-bath together with 10 drops of glacial acetic acid in 25 ml of benzene. After the dropwise addition of a solution of 250 mg of dicyanodichlorobenzoquinone in 10 ml of benzene, the mixture is warmed for an additional 15 minutes. The reaction mixture is subsequently cooled in an ice-bath and the separated solid is removed by filtration. The filtrate is shaken with 10% sodium carbonate solution. After separation of the organic phase the aqueous phase is extracted once with benzene. The combined organic phases are dried with anhydrous magnesium sulfate, filtered and evaporated under reduced pressure. The crystalline residue is recrystallized from ethyl acetate/n-hexane and there is obtained 1-(4-hydroxy-3,5-di-tert.-butylbenzylideneamino)imidazole of m.p. 173°.

EXAMPLE 14

(a) 15 ml of acetic anhydride and 7.5 ml of formic acid (98–100%) are mixed carefully at 0° and subsequently heated to 50° on a water-bath for 1 hour. The mixed anhydride formed is diluted with 25 ml of abs. tetrahydrofuran and 4.52 g of 1-(4-hydroxy-3,5-di-tert.-butylbenzylamino)imidazole are introduced in small portions into the solution obtained. The reaction mixture is left to stand at room temperature for 1 hour and evaporated under reduced pressure on a rotary evaporator. The residue is treated with a small amount of ice-cold water and saturated sodium bicarbonate is added up to a weakly alkaline reaction. After three-fold extraction with methylene chloride, the combined organic extracts are washed once with water and once with saturated sodium chloride solution, dried over anhydrous magnesium sulfate, filtered and evaporated. The residue is recrystallized from ethyl acetate/n-hexane and there is obtained 1-[N-formyl-N-(4-hydroxy-3,5-di-tert.-butylbenzyl)amino]imidazole of m.p. 167°.

(b) 3.30 g of 1-[N-formyl-N-(4-hydroxy-3,5-di-tert.-butylbenzyl)amino]imidazole are dissolved in 100 ml of absolute tetrahydrofuran. Into this solution there are injected at room temperature 20 ml of a 2 molar solution of borane-dimethyl sulfide complex [$BH_3.S(CH_3)_2$] in toluene. The reaction mixture is subsequently heated to gentle reflux for 2 hours, cooled to 0°, treated with 20 ml of absolute methanol and heated for an additional 30 minutes. The solvent is removed completely by evaporation under reduced pressure on a rotary evaporator. The residual crystalline solid is triturated with n-hexane, removed by filtration and vacuum-dried for a short period. Thereupon, the solid obtained is suspended in 50 ml of absolute methanol and hydrogen chloride is introduced carefully while stirring up to saturation, whereby a clear solution results with strong warming. This solution is heated to gentle reflux for 1 hour and then evaporated under reduced pressure on a rotary evaporator. The residue is treated with 25 ml of ice-cold water, whereupon saturated sodium bicarbonate solution is added to a weakly alkaline reaction and the mixture is extracted three times with 25 ml of methylene chloride each time. The combined methylene chloride extracts are washed once with a small amount of water and subsequently with saturated sodium chloride solution, dried over anhydrous magnesium sulfate, filtered and evaporated. The residue is recrystallized from ethyl acetate/n-hexane and there is obtained 1-[N-(4-hydroxy-3,5-di-tert.-butylbenzyl)-N-methylamino]imidazole of m.p. 139°.

EXAMPLE 15

(a) 0.6 g of 1-(4-hydroxy-3,5-di-tert.-butylbenzylamino)imidazole are dissolved in 5.3 ml of formic acid, 1.9 ml of acetic anhydride are added while cooling with ice and the mixture is left to stand overnight. Thereupon, the mixture is evaporated in a vacuum, water is added and the mixture is again evaporated. Water and methylene chloride are added to the crystalline residue and the mixture is neutralized (pH=7) with sodium bicarbonate solution. The organic phase is separated, dried and evaporated in a vacuum. The residue is stirred with ether and filtered. The 1-[N-formyl-N-(4-hydroxy-3,5-di-tert.-butylbenzyl)amino]imidazole which remains behind on the filter exhibits a m.p. of 169°–170°.

(b) The 1-[N-formyl-N-(4-hydroxy-3,5-di-tert.-butylbenzyl)amino]imidazole can be converted into 1-[N-(4-hydroxy-3,5-di-tert.-butylbenzyl)-N-methylamino]imidazole in accordance with the details in Example 14b).

EXAMPLE 16

(a) 680 mg of imidazole are suspended in a mixture of 4 ml of absolute N-methyl-2-pyrrolidone and 1 ml of absolute tetrahydrofuran. The suspension is cooled to −40°. A solution of 4.8 g of O-(2,4-dinitrophenyl)hydroxylamine in 8 ml of absolute N-methyl-2-pyrrolidone is slowly added dropwise while stirring within 30 minutes. The reaction mixture is left to stand at 20° for 18 hours, treated with 25 ml of water and 12 ml of 2N hydrochloric acid and extracted five times with 20 ml of ether each time. The acidic solution is stirred with active carbon for 15 minutes and filtered. After the addition of 3 ml of benzaldehyde, 5 ml of 2N hydrochloric acid and 30 ml of ether, the mixture is stirred for three hours while cooling with ice. The separated precipitate is removed by filtration and washed twice with water and once with ether. The thus-obtained crude product is reprecipitated from methanol/ether. There is obtained 1,3-bis(benzylideneamino)imidazolium chloride of melting point 193°–196°.

(b) 3.11 g of 1,3-bis(benzylideneamino)imidazolium chloride, 0.32 g of sulfur and 1.01 g of triethylamine are suspended in 20 ml of absolute pyridine, and the mixture is stirred at room temperature for 15 minutes. The reaction mixture is subsequently heated to boiling under reflux for a half hour. After cooling to room temperature, the mixture is treated with 100 ml of water. The resulting precipitate is removed by filtration under suction and washed three times with water and three times with ethanol. There is obtained pale yellow 1,3-bis(benzylideneamino)-1,3-dihydro-2H-imidazole-2-thione of melting point 215°–218°.

(c) 3.06 g of 1,3-bis(benzylideneamino)-1,3-dihydro-2H-imidazole-2-thione in 100 ml of absolute methylene chloride are treated with 1.47 g of trimethyloxonium tetrafluoroborate. The mixture is stirred at room temperature for 3 hours and the resulting precipitate is removed by filtration under suction. From the filtrate, by the addition of diethyl ether, there is precipitated a additional portion of the desired product which, together with the first portion, is washed once with water, once with cold methanol and three times with diethyl ether and subsequently reprecipitated from acetonitrile/diethyl ether. There is obtained colorless 1,3-bis(benzylideneamino)-2-(methylthio)imidazolium tetrafluoroborate of melting point 215°–220° (decomposition).

(d) 4.1 g of 1,3-bis(benzylideneamino)-2-(methylthio)imidazolium tetrafluoroborate in 25 ml of absolute acetonitrile are treated under an argon atmosphere with 1.45 g of absolute morpholine, whereby the evolution of methylmercaptan sets in immediately and solution occurs. The solution is left to stir overnight at room temperature until the cleavage of methylmercaptan is complete. The resulting colorless precipitate is removed by filtration. The filtrate is treated with 30 ml of diethyl ether and again filtered. The two filter residues are combined and reprecipitated from acetonitrile/ether. There is obtained 1,3-bis(benzylideneamino)-2-morpholinoimidazolium tetrafluoroborate in the form of colorless crystals of m.p. 244°–247° (dec.).

(e) 4.47 g of 1,3-bis(benylideneamino)-2-morpholinoimidazolium tetrafluoroborate are suspended in 50 ml of methanol. A solution of 1.3 g of potassium cyanide in 20 ml of water is added dropwise within 15 minutes while cooling in an ice-bath, whereby a yellow solution results. The solution is stirred at room temperature for an additional 15 minutes, 150 ml of water are added and the mixture is extracted three times with 30 ml of methylene chloride each time. The combined methylene chloride extracts are dried over sodium sulfate, filtered and evaporated in a vacuum. The yellow oil which remains behind as the residue is treated with 70 ml of ice-cold water. Then the mixture is acidified (pH about 1) with 2N hydrochloric acid and subsequently extracted three times with diethyl ether. The colorless, acidic-aqueous phase is treated with 2N sodium hydroxide solution up to an alkaline reaction (pH about 8–9). The resulting pale yellow precipitate is removed by filtration and reprecipitated from methanol/water. There is obtained 1-benzylideneamino-2-morpholinoimidazole of m.p. 59°–61°.

(f) 3.85 g of 1-benzylideneamino-2-morpholinoimidazole are dissolved in 20 ml of 1N hydrochloric acid and subjected to a steam distillation until benzaldehyde no longer passes over. The residual colorless acidic solution is concentrated to about 10 ml, treated with 5N sodium hydroxide solution while cooling up to an alkaline reaction and then saturated with sodium chloride. The mixture is extracted five times with 25 ml of methylene chloride each time, the combined organic phases are dried over sodium sulfate, filtered and the solvent is removed by evaporation in a vacuum. The colorless, crystalline 1-amino-1-morpholinoimidazole which remains behind as the residue is already sufficiently pure for further processing. A sample purified by recrystallization from n-hexane/ethyl acetate or by sublimation exhibits a m.p. of 150°–151° (sublimation from 120°).

(g) 1.18 g of 1-amino-2-morpholinoimidazole are dissolved in 50 ml of ethanol and treated with 3.5 ml of 2N hydrochloric acid. After the addition of 1.65 g of 4-hydroxy-3,5-di-tert.-butylbenzaldehyde, the reaction mixture is stirred at room temperature overnight. The solvent is subsequently removed by evaporation in a vacuum. The residue is treated with 20 ml of water and saturated sodium carbonate solution is added up to an alkaline reaction. The separated, colorless product is removed by filtration and purified by column chromatography (eluent methylene chloride/methanol 10%). By recrystallization from water/methanol, there is obtained pure 1-(4-hydroxy-3,5-di-tert.-butylbenzylideneamino)-2-morpholinoimidazole of m.p. 185°–187°.

EXAMPLE 17

1.92 g of 1-(4-hydroxy-3,5-di-tert.-butylbenzylideneamino)-2-morpholinoimidazole are dissolved in 30 ml of glacial acetic acid and treated portionwise within 30 minutes with 0.7 g of 90% sodium cyanoborohydride. The reaction mixture is stirred overnight. The solvent is removed by evaporation in a vacuum and the residue is treated with 20 ml of water. Saturated sodium carbonate solution is added up to an alkaline reaction and the mixture is extracted three times with 20 ml of methylene chloride each time. The organic phases are combined, dried over sodium sulfate, filtered and evaporated. The residue is boiled up briefly with 20 ml of n-hexane. After cooling, the crystalline colorless product is removed by filtration and recrystallized from methanol/water. There is obtained 1-(4-hydroxy-3,5-di-tert.-butylbenzylamino)-2-morpholinoimidazole of m.p. 161°-163°.

EXAMPLE 18

(a) 12.5 g of 2-isopropylimidazole are suspended in 35 ml of water and treated within 30 minutes while stirring with a solution, prepared at 0°, from 12.5 g of hydroxylamine O-sulfonic acid and 9.25 g of sodium bicarbonate in 75 ml of ice-water. After stirring at room temperature for 20 hours, the mixture is acidified with 32.5 ml of 2N hydrochloric acid. A solution of 7.75 g of benzaldehyde in 25 ml of ether is added and the mixture is stirred at room temperature for 6 hours. After removal of the ether by evaporation, the residue is extracted thoroughly with methylene chloride. The extract is dried over sodium sulphate and evaporated. The residue is crystallized by the addition of methylene chloride. After recrystallization from methylene chloride there is obtained 1-benzylideneamino-2-isopropylimidazolium benzaldoxime O-sulfonate of m.p. 147°-148°.

5.3 g of the above salt are suspended in 100 ml of methylene chloride, and 70 ml of saturated sodium hydrogen carbonate solution are added. The product is extracted with methylene chloride and crystallized from ether/petroleum ether. 1-Benzylideneamino-2-isopropylimidazole of m.p. 65°-66° is obtained.

(b) A mixture of 1 g of 1-benzylideneamino-2-isopropylimidazole and 50 ml of 1N hydrochloric acid is subjected to a steam distillation until benzaldehyde no longer passes over. The residual solution is evaporated in a vacuum. Methanol and benzene are added to the residue. The mixture is evaporated, methanol and benzene are again added and the mixture is again evaporated. Crude 1-amino-2-isopropylimidazole hydrochloride is obtained.

(c) 0.65 g of the above crude 1-amino-2-isopropylimidazole hydrochloride is dissolved in 30 ml of ethanol, 0.94 g of 4-hydroxy-3,5-di-tert.-butylbenzaldehyde is added and the mixture is stirred at room temperature for 2 hours. The resulting solution is evaporated in a vacuum. The residue is partitioned between methylene chloride and water. The aqueous phase is treated with sodium bicarbonate solution up to a neutral reaction (pH=7) and the methylene chloride phase is separated, dried, filtered and evaporated. The residue is stirred with ether, whereupon the solid is removed by filtration and dried; there is obtained 1-(4-hydroxy-3,5-di-tert.-butylbenzylideneamino)-2-isopropylimidazole of m.p. 159°-160°.

EXAMPLE 19

(a) 71 g of hydroxylamine O-sulfonic acid are dissolved in 420 ml of ice-water and neutralized by the addition of 54 g of sodium bicarbonate. The solution obtained is added dropwise within 30 minutes to a solution of 25.8 g of 4(5)-methylimidazole in 320 ml of water, whereby the pH is held at 9.5 by the constant addition (autotitrator) of 1N sodium hydroxide solution. The mixture is stirred at room temperature overnight, conc. hydrochloric acid is added up to an acidic reaction (pH=1.5), and the mixture is treated with a solution of 64 ml of benzaldehyde in 200 ml of ether and stirred at room temperature for 6 hours, whereby crystallization occurs already after about 30 minutes.

The separated solid is removed by filtration, washed with water and ether and dried at 60°. There is obtained 1,3-bis-(benzylideneamino)-4(5)-methylimidazolium chloride of m.p. 137°-139° (dec.). The filtrate is adjusted to pH 6 by the addition of 2N sodium hydroxide solution. The separated oil is extracted with ethyl acetate. The ethyl acetate phase is separated, washed with water, dried and evaporated in a vacuum. The oily residue is dissolved in 100 ml of hot isopropyl ether. The crystals which separate upon cooling are removed by filtration and washed firstly with isopropyl ether and then with petroleum ether and there is obtained 1-benzylideneamino-4-methylimidazole of m.p. 91°-93°.

(b) 5.7 g of 1-benzylideneamino-4-methylimidazole in 50 ml of water and 30 ml of 2N hydrochloric acid are subjected to a steam distillation until benzaldehyde no longer passes over. The residual solution is filtered over charcoal and evaporated in a vacuum. The residue is treated with methanol and toluene and the resulting mixture is evaporated. Methanol and toluene are again added and the mixture is again evaporated. The residue is taken up in ethanol and crystallization is brought about by the addition of ether. The separated solid is removed by filtration, washed with ether and hexane and dried at 60° in a vacuum. There is obtained 1-amino-4-methylimidazole hydrochloride of m.p. 114°-155°.

(c) 3.5 g of 1-amino-4-methylimidazole hydrochloride are dissolved in 200 ml of ethanol. 6.2 g of 4-hydroxy-3,5-di-tert.-butylbenzaldehyde are added and the mixture is stirred at room temperature overnight. The solution obtained is then evaporated in a vacuum. The residue is treated with 150 ml of methylene chloride and 150 ml of water, stirred and saturated sodium bicarbonate solution is added up to a neutral reaction (pH=7). The methylene chloride phase is separated and the aqueous phase is extracted with 50 ml of methylene chloride. The methylene chloride phases are combined, washed once with 10% sodium chloride solution, dried and evaporated. The residue is triturated with cold ether. The solid is removed by filtration, washed with ether and n-hexane and dried at 70° in a vacuum. There is obtained 1-(4-hydroxy-3,5-di-tert.-butylbenzylideneamino)-4-methylimidazole of m.p. 150°-151°.

EXAMPLE 20

6.1 g of 1-(4-hydroxy-3,5-di-tert.-butylbenzylideneamino)-4-methylimidazole are hydrogenated at normal pressure and room temperature in 100 ml of methanol, 21 ml of 1N hydrochloric acid and 30 ml of water in the presence of palladium-carbon. After 500 ml of hydrogen have been taken up, the mixture is filtered. The filtrate is evaporated to a volume of 50 ml. Then, 50 ml of water are added and the mixture is treated with saturated sodium bicarbonate solution up to a neutral reaction (pH=7). The separated crystals are removed by filtration, and taken up with methylene chloride. The methylene chloride solution is washed once with water, dried and evaporated. The residue is triturated with cold ether. Thereafter the solid is removed by filtration, washed with ether and n-hexane and dried at 60° in a vacuum. There is obtained 1-(4-hydroxy-3,5-di-tert.-butylbenzylamino)-4-methylimidazole of m.p. 150°-151°.

EXAMPLE 21

(a) 25 g of 2-propylimidazole are suspended in 70 ml of water and treated within 20 minutes while stirring with a solution, prepared at 0°, from 25 g of hydroxylamine O-sulfonic acid and 18.5 g of sodium bicarbonate in 150 ml of water. After stirring at room temperature for 20 hours, the mixture is acidified with 65 ml of 2N hydrochloric acid. A solution of 15.5 g of benzaldehyde in 50 ml of ether is added and the mixture is stirred at room temperature for 6 hours. The white crystals formed are removed by filtration. The filtrate is treated as described below.

The crystals are dissolved in methylene chloride. The solution is dried over sodium sulfate, filtered and concentrated. The residue is crystallized by the addition of ether. After recrystallization from ethanol, there is obtained 1,3-bis(benzylideneamino)-2-propylimidazolium benzaldoxime O-sulfonate of m.p. 143°–145°.

The above filtrate is washed with ether, treated with 60 ml of 3N sodium hydroxide solution and extracted with methylene chloride. After drying the extract over sodium sulfate, filtration and removal of the methylene chloride by evaporation, there is obtained a reddish oil from which by chromatography on silica gel (particle size 0.063–0.2 mm) by means of methylene chloride/methanol (99:1%) there is obtained 1-benzylideneamino-2-propylimidazole of m.p. 61°–62°.

(b) A suspension of 14 g of 1-benzylideneamino-2-propylimidazole in 113 ml of water and 79 ml of 2N hydrochloric acid is subjected to a steam distillation until benzaldehyde no longer passes over. The residual, slightly turbid solution is cooled and evaporated in a vacuum. Methanol and benzene are added to the oily residue. The mixture is evaporated, 30 ml of ethanol are added and the solution obtained is treated with ether until turbidity begins. After cooling the separated crystals are removed by filtration, washed with ether and n-hexane and dried at 60° in a vacuum and 1-amino-2-propylimidazole hydrochloride of m.p. 108°–109° is obtained.

(c) 6.47 g of 1-amino-2-propylimidazole hydrochloride are dissolved in 300 ml of ethanol, and 3.5 g of 4-hydroxy-3,5-di-tert.-butylbenzaldehyde are added. The mixture is stirred at room temperature for 3 hours and the solution obtained is evaporated. The residue is treated with 150 ml of water and 150 ml of methylene chloride, and saturated sodium bicarbonate solution is added while stirring up to a neutral reaction (pH=7). The methylene chloride phase is separated. The aqueous phase is extracted once with 50 ml of methylene chloride. The methylene chloride solutions are combined, dried and evaporated. The residue is triturated with ether, and the solid is removed by filtration and dried at 60° in a vacuum. There is obtained 1-(4-hydroxy-3,5-di-tert.-butylbenzylideneamino)-2-propylimidazole of m.p. 160°–161°.

EXAMPLE 22

9.9 g of 1-(4-hydroxy-3,5-di-tert.-butylbenzylideneamino)-2-propylimidazole are hydrogenated at normal pressure and room temperature in 200 ml of methanol and 29 ml of 1N hydrochloric acid in the presence of 1 g of a palladium catalyst (5% on carbon). After 700 ml of hydrogen have been taken up, the catalyst is removed by filtration and the filtrate is evaporated. The residue is taken up with 100 ml of water, and saturated sodium bicarbonate solution is added up to a neutral reaction (pH=7). The separated crystals are removed by filtration and taken up in 300 ml of methylene chloride. The methylene chloride solution is washed once with water, dried and evaporated. The residue is dissolved in 50 ml of hot isopropyl ether. The crystals which separate upon cooling are removed by filtration, washed with isopropyl ether and n-hexane and dried at 60° in a vacuum. There is obtained 1-(4-hydroxy-3,5-di-tert.-butylbenzylamino)-2-propylimidazole of m.p. 122°–123°.

EXAMPLE A

Suppositories of the following composition are prepared in the usual and known manner:

| | |
|---|---|
| 1-(4-Hydroxy-3,5-di-tert.-butylbenzyl-amino)imidazole | 0.025 g |
| Hydrogenated coconut oil | 1.230 g |
| Carnauba wax | 0.045 g |
| Total weight | 1.300 g |

EXAMPLE B

Tablets of the following composition are prepared in the usual and known manner:

| | Per tablet |
|---|---|
| 1-(4-Hydroxy-3,5-di-tert.-butylbenzyl-amino)imidazole | 25.00 mg |
| Lactose | 64.50 mg |
| Maize starch | 10.00 mg |
| Magnesium stearate | 0.50 mg |
| Total weight | 100.00 mg |

EXAMPLE C

Capsules of the following composition are prepared in the usual and known manner:

| | Per capsule |
|---|---|
| 1-(4-Hydroxy-3,5-di-tert.-butylbenzyl-amino)imidazole | 50 mg |
| Lactose | 125 mg |
| Maize starch | 30 mg |
| Talc | 5 mg |
| Total weight of the capsule filling | 210 mg |

We claim:
1. A compound of the formula

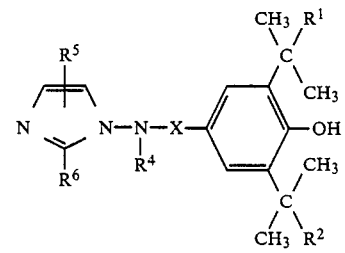

wherein $R^1$ and $R^2$ each is lower alkyl, X is a residue of the formula

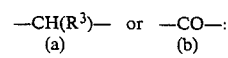

$R^3$ is hydrogen and $R^4$ is hydrogen or lower alkyl or $R^3$ and $R^4$ taken together are an additional carbon-nitrogen bond; $R^5$ is hydrogen or lower alkyl; $R^6$ is hydrogen, lower alkyl, lower alkylthio or a residue of the formula $-NR^7R^8$; and $R^7$ and $R^8$ each is lower alkyl or together with the nitrogen atom are a 5- or 6-membered saturated heterocycle selected from the group consisting of morpholino, piperidino and pyrrolidino, or a pharmaceutically acceptable acid addition salt thereof.

2. A compound according to claim 1, wherein $R^1$ and $R^2$ each is methyl.

3. A compound according to claim 2, wherein $R^5$ is hydrogen or methyl in the 4-position.

4. A compound according to of claim 3, wherein $R^6$ is hydrogen, methyl, n-propyl, isopropyl, methylmercapto or morpholino.

5. A compound according to claim 4, wherein $R^3$ is hydrogen and $R^4$ is hydrogen or methyl or $R^3$ and $R^4$ taken together are an additional carbon-nitrogen bond.

6. A compound according to claim 1, 1-(4-hydroxy-3,5-di-tert.-butylbenzylamino)imidazole.

7. A compound according to claim 1, 1-(4-hydroxy-3,5-di-tert.-butylbenzylideneamino)-2-methylimidazole.

8. A compound according to claim 1, 1-(4-hydroxy-3,5-di-tert.-butylbenzylideneamino)imidazole.

9. A compound according to claim 1, 1-(4-hydroxy-3,5-di-tert.-butylbenzylamino)-2-methylimidazole.

10. A compound according to claim 1, 1-(4-hydroxy-3,5-di-tert.-butylbenzylamino)-2-propylimidazole.

11. A compound according to claim 1, 1-(4-hydroxy-3,5-di-tert.-butylbenzylamino)-2-methylmercaptoimidazole.

12. A compound selected from the group consisting of 1-(4-hydroxy-3,5-di-tert.-butylbenzoylamino)-2-methylimidazole;
   1-(4-hydroxy-3,5-di-tert.-butylbenzoylamino)imidazole;
   1-(4-hydroxy-3,5-di-tert.-butylbenzylideneamino)-2-morpholinoimidazole;
   1-(4-hydroxy-3,5-di-tert.-butylbenzylamino)-2-morpholinoimidazole;
   1-(4-hydroxy-3,5-di-tert.-butylbenzylideneamino)-2-isopropylimidazole;
   1-(4-hydroxy-3,5-di-tert.-butylbenzylideneamino)-4-methylimidazole;
   1-(4-hydroxy-3,5-di-tert.-butylbenzylamino)-4-methylimidazole;
   1-(4-hydroxy-3,5-di-tert.-butylbenzylideneamino)-2-propylimidazole; and
   1-[N-(4-hydroxy-3,5-di-tert.-butylbenzyl)-N-methylamino]imidazole.

13. A pharmaceutical composition comprising an anti-inflammatorily effective amount of a compound of the formula

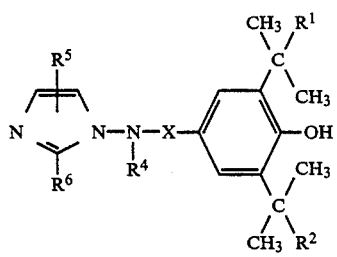

wherein $R^1$ and $R^2$ each is lower alkyl, X is a residue of the formula

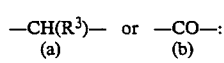

$R^3$ is hydrogen and $R^4$ is hydrogen or lower alkyl or $R^3$ and $R^4$ taken together are an additional carbon-nitrogen bond; $R^5$ is hydrogen or lower alkyl; $R^6$ is hydrogen, lower alkyl, lower alkylthio or a residue of the formula $-NR^7R^8$; and $R^7$ and $R^8$ each is lower alkyl or together with the nitrogen atom are a 5- or 6-membered saturated heterocycle selected from the group consisting of morpholino, piperidino and pyrrolidino, or a pharmaceutically acceptable acid addition salt thereof, and an inert carrier material.

14. A pharmaceutical composition according to claim 13, wherein the compound of formula I is 1-(4-hydroxy-3,5-di-tert.-butylbenzylamino)imidazole.

15. A pharmaceutical composition according to claim 13, wherein the compound of formula I is 1-(4-hydroxy-3,5-di-tert.-butylbenzylideneamino)-2-methylimidazole.

16. A pharmaceutical composition according to claim 13, wherein the compound of formula I is 1-(4-hydroxy-3,5-di-tert.-butylbenzylideneamino)imidazole.

17. A pharmaceutical composition according to claim 13, wherein the compound of formula I is 1-(4-hydroxy-3,5-di-tert.-butylbenzylamino)-2-methylimidazole.

18. A pharmaceutical composition according to claim 13, wherein the compound of formula I is 1-(4-hydroxy-3,5-di-tert.-butylbenzylamino)-2-propylimidazole.

19. A pharmaceutical composition according to claim 13, wherein the compound of formula I is 1-(4-hydroxy-3,5-di-tert.-butylbenzylamino)-2-methylmercaptoimidazole.

20. A method of treating inflammation which comprises administering to a host requiring such treatment an effective amount of a compound of the formula

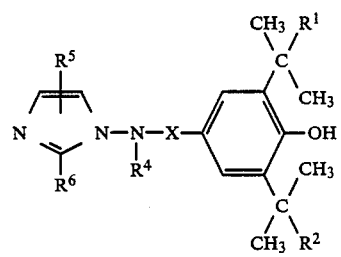

wherein $R^1$ and $R^2$ each is lower alkyl, X is a residue of the formula

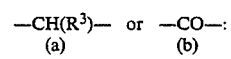

$R^3$ is hydrogen and $R^4$ is hydrogen or lower alkyl or $R^3$ and $R^4$ taken together are an additional carbon-nitrogen bond; $R^5$ is hydrogen or lower alkyl; $R^6$ is hydrogen, lower alkyl, lower alkylthio or a residue of the formula $-NR^7R^8$; and $R^7$ and $R^8$ each is lower alkyl or together with the nitrogen atom are a 5- or 6-membered saturated heterocycle selected from the group consisting of morpholino, piperidino and pyrrolidino, or a pharmaceutically acceptable acid addition salt thereof.

21. A method according to claim 20, wherein the compound of formula I is 1-(4-hydroxy-3,5-di-tert.-butylbenzylamino)imidazole.

22. A method according to claim 20, wherein the compound of formula I is 1-(4-hydroxy-3,5-di-tert.-butylbenzylideneamino)-2-methylimidazole.

23. A method according to claim 20, wherein the compound of formula I is 1-(4-hydroxy-3,5-di-tert.-butylbenzylideneamino)imidazole.

24. A method according to claim 20, wherein the compound of formula I is 1-(4-hydroxy-3,5-di-tert.-butylbenzylamino)-2-methylimidazole.

25. A method according to claim 20, wherein the compound of formula I is 1-(4-hydroxy-3,5-di-tert.-butylbenzylamino)-2-propylimidazole.

26. A method according to claim 20, wherein the compound of formula I is 1-(4-hydroxy-3,5-di-tert.-butylbenzylamino)-2-methylmercaptoimidazole.

* * * * *